United States Patent [19]

Arnold et al.

[11] Patent Number: 5,714,354
[45] Date of Patent: Feb. 3, 1998

[54] ALCOHOL-FREE PNEUMOCOCCAL POLYSACCHARIDE PURIFICATION PROCESS

[75] Inventors: Frank Josef Arnold, Newfoundland, Pa.; Michael Soika, Spring Valley, N.Y.

[73] Assignee: American Home Products Corporation, Madison, N.J.

[21] Appl. No.: 471,439

[22] Filed: Jun. 6, 1995

[51] Int. Cl.$^6$ .................. C12P 19/04; A61K 39/09; A61K 31/715; C08B 37/00
[52] U.S. Cl. .................. 435/101; 536/123.1; 514/54; 424/244.1
[58] Field of Search .................. 435/101; 514/54; 536/123.1; 424/244.1

[56] References Cited

U.S. PATENT DOCUMENTS

| | | | |
|---|---|---|---|
| 4,220,717 | 9/1980 | Kuo | 435/101 |
| 4,242,501 | 12/1980 | Cano et al. | 536/1 |
| 4,686,102 | 8/1987 | Ritchey et al. | 424/92 |

FOREIGN PATENT DOCUMENTS

| | | |
|---|---|---|
| 0 002 404 A1 | 6/1979 | European Pat. Off. |
| 0072513 | 3/1989 | European Pat. Off. |

*Primary Examiner*—Leon B. Lankford, Jr.
*Assistant Examiner*—Francisco C. Prats
*Attorney, Agent, or Firm*—T. S. Szatkowski

[57] ABSTRACT

An alcohol-free process for purifying pneumococcal capsular polysaccharide (substantially absent "C" polysaccharide) of pneumococcal types (Danish designation), 1, 2, 3, 4, 5, 6B, 7F, 8, 9N, 9V, 10A, 11A, 12F, 14, 15B, 17F, 18C, 19A, 19F, 20, 22F, 23F and 33F using a cationic detergent, for example, hexadecyl-trimethylammonium bromide.

10 Claims, 4 Drawing Sheets

SEC-HPLC ANALYSIS OF T9V-0012 CRUDE LYSATE

PURITY:
UV280—18.3 OD/G POLYSACCHARIDE
UV260—30.2 OD/G POLYSACCHARIDE

SEC-HPLC ANALYSIS OF T9V-0012 FOLLOWING 100K CONCENTRATION AND DIAFILTRATION

PURITY:
UV280— 7.1 OD/G POLYSACCHARIDE
UV260—12.7 OD/G POLYSACCHARIDE

SEC-HPLC ANALYSIS OF CTV PRECIPITATED T9V-0012

PURITY:
UV280— 0.4 OD/G POLYSACCHARIDE
UV260— 0.3 OD/G POLYSACCHARIDE

SEC-HPLC ANALYSIS OF THE KI TREATED T9V-0012 PRECIPITATE

PURITY:
UV280— 0.16 OD/G POLYSACCHARIDE
UV260— 0.3 OD/G POLYSACCHARIDE

SEC-HPLC ANALYSIS OF CUNO NORIT TREATED T9V-0012

PURITY:
UV280— 0.03 OD/G POLYSACCHARIDE
UV260— 0.3 OD/G POLYSACCHARIDE

SEC-HPLC ANALYSIS OF HA PURIFIED T9V-0012

PURITY:
UV280— 0.007 OD/G POLYSACCHARIDE (0.09% PROTEIN)
UV260— 0.008 OD/G POLYSACCHARIDE (0.001% DNA)

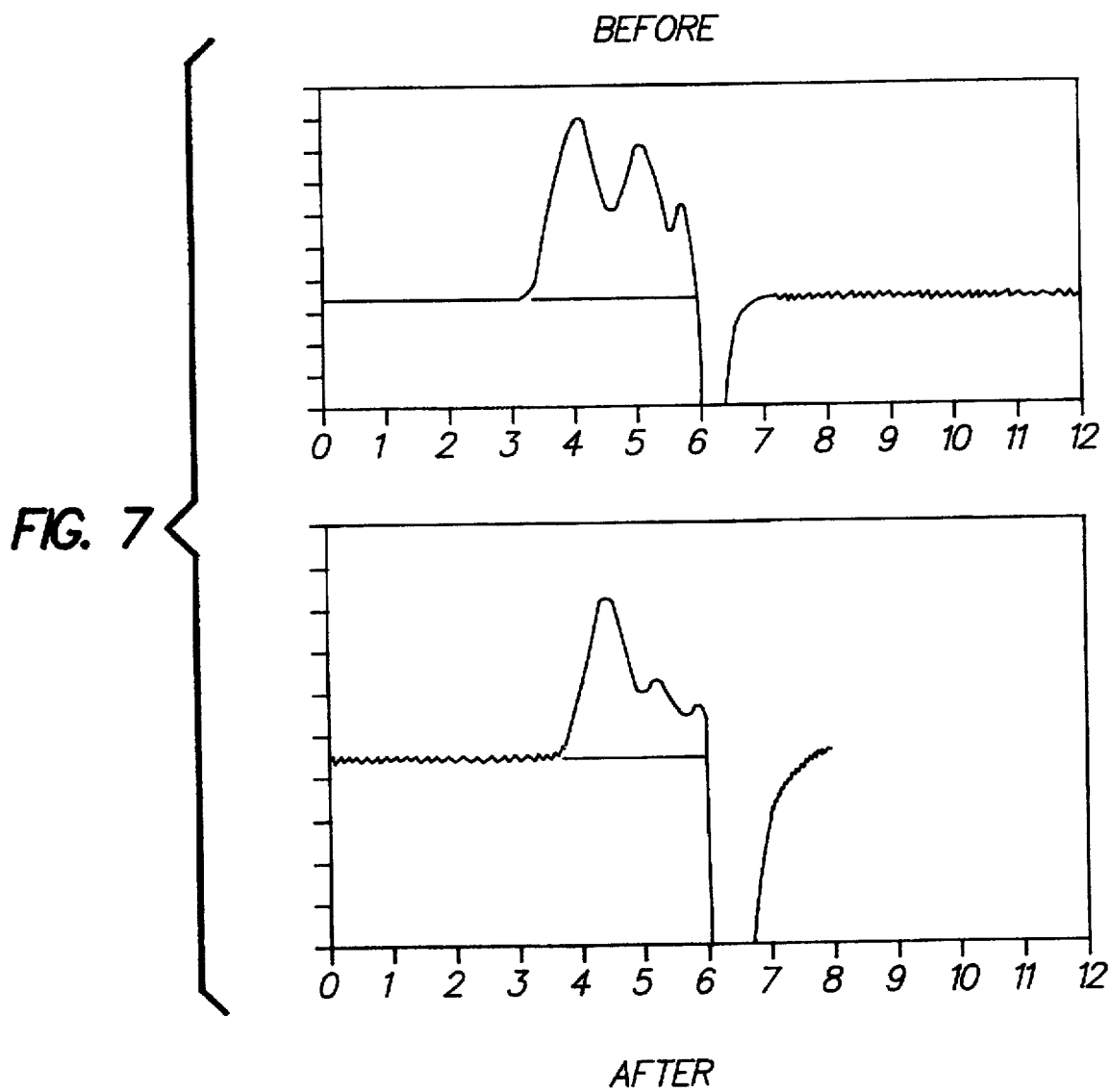
FIG. 7 SEC-HPLC ANALYSIS OF T33F-0012 BEFORE AND AFTER ANION-EXCHANGE CROMATOGRAPHY

ALCOHOL-FREE PNEUMOCOCCAL POLYSACCHARIDE PURIFICATION PROCESS

SUMMARY OF THE INVENTION

The invention is an alcohol free method for the purification of pneumococcal polysaccharides which are used in the preparation of polysaccharide vaccines. Cationic detergent (hexadecyl-trimethylammonium bromide) is used to precipitate 20 of the 23 serotypes. The remainder of the process utilizes chromatographic separation of contaminants from the polysaccharides by activated carbon filtration, hydroxyapatite chromatography and anion exchange chromatography. The process is a generic process to purify pneumococcal polysaccharides. For the three serotypes that do not precipitate with the detergent, a modified process is applied. This process can purify polysaccharides with 75% less time requiring low cost materials in the process and no specialized facilities or disposal of hazardous materials.

DESCRIPTION OF THE DRAWINGS

FIG. 7 is a SEC-HPLC analysis of T33F-0012 before and after anion-exchange chromatography.

DETAILED DESCRIPTION

Figure 1:
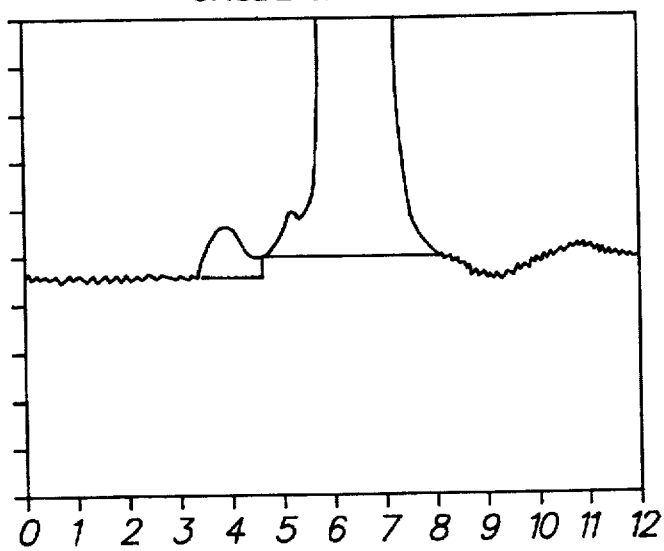
FIG. 1 is a size exclusion high performance liquid chromatography (HPLC) (SEC-HPLC) analysis of T9V-0012 (serotype 9V) crude lysate.

Due to operational problems that result from the use of alcohol during pneumococcal polysaccharide purification and the extremely long process time for current processes, we have investigated alternatives to the use of alcohol. We have investigated using bulk chromatographic steps such as cation/anion exchange and hydrophobic/hydrophilic interaction to initially purify the polysaccharides. However, these methods proved to be ineffective in preparing a high quality product with high yields. We have discovered an alcohol-free process using cationic detergents, for example, hexadecyl 1-trimethylammonium bromide, to remove protein and nucleic acid contaminants via precipitation. Some of the polysaccharides are not precipitated with the detergent by using very low concentrations while the remaining serotypes are coprecipitated with the contaminants but are subsequently resuspended into buffer that prevents the contaminants from resolubilizing. For the types that precipitate, it has been historically troublesome to solubilize the polysaccharides from the detergent.

We found that all pneumococcal polysaccharide types precipitate with hexadecyl-trimethylammonium bromide (1-4%) with the exception of pneumococcal polysaccharide types 7F, 14 and 33F. This single precipitation step is shown to be more efficient at processing pneumococcal polysaccharides to remove C-polysaccharide and other contaminants than several cycles of alcohol fractionation. The remainder of the purification process requires treatment with activated carbon filters followed by hydroxy apatite chromatography. This greatly simplified procedure produces polysaccharide of high purity. For serotypes 7F, 14 and 33F that do not precipitate with the detergent, additional processing with anion exchange chromatography produces material of high purity as well. The invention is an alcohol free purification process for pneumococcal polysaccharides that meets all of the release test specifications required for the adult vaccine for pneumococcal disease containing the 23 serotypes of Table 1, below.

Pneumococcal cultures of each type useful in this invention are stored and available worldwide from a great number of culture libraries. The American Type Culture Collection (ATCC), 12301 Parklawn Dr., Rockville, Md., U.S.A. 20852, lists all of the pneumococcal types of this invention as being freely available.

The 1978 ATCC catalogue designates these types as follows:

TABLE 1

| Danish Type Nomenclature | Catalogue Number |
|---|---|
| 1 | 6301 |
| 2 | 6302 |
| 3 | 6303 |
| 4 | 6304 |
| 5 | |
| 6B | 6326 |
| 7F | 10351 |
| 8 | 6308 |
| 9N | 6309 |
| 9V | |
| 10A | |
| 11A | |
| 12F | 6312 |
| 14 | 6314 |
| 15B | |
| 17F | |
| 18C | 10356 |
| 19A | |
| 19F | 6319 |
| 20 | 6320 |
| 22F | |
| 23F | 6323 |
| 33F | |

The invention is a process for preparing a purified pneumococcal polysaccharide which comprises:

1) lysing with deoxycholate a fermentation media, serotypes 1, 2, 3, 4, 5, 6B, 8, 9N, 9V, 10A, 11A, 12F, 15B, F, 18C, 19A, 19F, 20, 22F and 23F containing s. pneumococcal bacteria thereby producing a lysate containing a polysaccharide solution and solid cell debri;

2) clarifying an aqueous cell lysate by separating solids from the polysaccharide solution;

3) concentrating the polysaccharide solution by ultrafiltration to remove low molecular weight contaminants to form a solution of concentrated polysaccharide;

4) precipitating the concentrated polysaccharide solution with cationic detergent, for example, hexadecyl-trimethylammonium bromide, to form a partially purified polysaccharide pellet;

5) washing the pellet in buffer which contains the detergent to remove soluble contaminants;

6) collecting the resulting polysaccharide pellet;

7) solubilizing the polysaccharide pellet in a saline solution;

8) clarifying the polysaccharide solution to remove insoluble protein and nucleic acids;

9) adding potassium iodide to the polysaccharide solution to precipitate the detergent in a detergent-potassium iodide salt complex;

10) clarifying the polysaccharide solution by ultrafiltration; and 11) lyophilizing the polysaccharide solution; and a process for preparing a purified pneumococcal polysaccharide for serotypes 7F, 14 and 33F which comprises:

1) lysing with deoxycholate a fermentation media, containing s. pneumococcal bacteria, thereby producing a lysate containing a polysaccharide solution and solid cell debri;

2) clarifying an aqueous cell lysate by separating solids from the polysaccharide solution;

3) concentrating the polysaccharide solution by ultrafiltration to remove low molecular weight contaminants to form a solution of concentrated polysaccharide;

4) precipitating the protein and nucleic acid contaminants from the concentrated polysaccharide solution with a cationic detergent, for example, hexadecyltrimethylammonium bromide to form a partially purified polysaccharide solution;

5) clarifying the polysaccharide solution to remove insoluble nucleic acids and proteins;

6) recirculating the polysaccharide solution through an anion exchange column;

7) washing the column with 4 to 5 column volumes of buffer;

8) adding sodium or potassium iodide to the polysaccharide solution to precipitate the detergent in a detergent-potassium iodide salt complex;

9) clarifying the polysaccharide solution by ultrafiltration; and 10) lyophilizing the polysaccharide solution.

The flowsheets 1 and 2, below, illustrate the procedure performed separately on each of the 23 s. pneumococcal serotypes. Each individual serotype is purified as outlined. Final purified polysaccharides are then used to formulate a 23 valent vaccine. The cationic detergent of the flowsheets is the hexadecyltrimethylammonium bromide marketed under the trademark Cetavalon® (CTV).

Flowsheet 1

Pneumo Process Flow for Alcohol Free Purification

Applied to serotypes:

1, 2, 3, 4, 5, 6B, 8, 9V, 10A, 11A, 12F, 15B, 17F, 18C, 19A, 19F, 20, 22F and 23F

DAY 1

Cell lysate 2L(0.5 mg/ml polysacc. in crude)

Clarification (centrifugation 9K, 30 minutes), Discard Pellet

100K Conc.10x & Diafilter (2.5L 25mM sodium acetate or 12.5 mM

-continued
Flowsheet 1 sodium phospate, pH 6.8)

CTV (HB) precipitation (1–3% final conc., >1 hour)*

Collect pellet (centrifugation 9K, 30 minutes or filter on 10sp CUNO zeta plus)

DAY 2

Resuspend pellet by polytron or recirculate through filter in 1% CTV (25 mM sodium acetate) to wash pellet*

Remove soluble contaminants (centrifugation 9K, 30 minutes)

Collect pellet-resuspend in 200 ml (0.25M NaCl, 0.35M NaCl for T3)

Clarify resuspended polysaccharide (centrifugation 9K, 30 minutes) Removes insoluble nucleic acid

0.5% KI addition (remove CTV, centrifuge or filter)

DAY 3

CUNO Norit Filtration (4% carbon/0.5 mg/ml poly in crude)

Recirculate for 30 minutes

25 mM phosphate pH 6.8 added polysaccharide solution

Pass Through 50–100 ml HA Column

Recirculate 30 minutes

Wash column with 4–5 column volumes of phosphate buffer

Flowsheet 1 -continued

Concentrate 5-fold and diafilter into water for lyo

↓

*T23F requires 4% CTV

Flowsheet 2

Pneumo Process Flow for Alcohol Free Purification

Modified for serotypes 7F, 14 & 33F

DAY 1

Cell lysate 2L

↓

Clarification (centrifugation 9K, 30 minutes), Discard Pellet

↓

100K Conc.10 × & Diafilter(2.5 L 25 mM sodium acetate, pH 6.8)

↓

CTV (HB) precipitation (1-2% final conc., >1 hour)

↓

Clarification (entrifugation 9K, 30 minutes), Discard Pellet

↓

DAY 2

Pass CTV supernatant through 50-100 ml Q-Anion Exchange

Column (Optional depending on growth media-HY Soy may not require)

Recirculate 30 minutes

↓

Wash column with 4-5 column volumes of phosphate buffer

↓

Add 0.5% KI addition (remove CTV, centrifuge or filter)

↓

DAY 3

CUNO Norit Filtration (4-8% carbon/0.5 mg/ml poly in crude)

Flowsheet 2 -continued

Recirculate for 30 minutes

↓

25 mM phosphate pH 6.8 added polysaccharide solution

↓

Pass Through 25-50 ml HA Column

Recirculate 30 minutes

↓

Wash column with 4-5 column volumes of phosphate buffer

↓

Concentrate 5-fold and diafilter into water for lyophilization

Details of the Process
(Refer to Flowsheets 1 and 2)
Crude Lysate Concentration and Diafiltration Clarified crude lysate of the 23 serotypes of the process (polysaccharide content ranges from 0.3-0.5 mg/ml) is concentrated 10-fold (2L to 200 ml) in a 100K molecular weight cutoff hollow fiber membrane to a final polysaccharide concentration not to exceed 5 mg/ml (AG Technologies or equivalent) with a recirculation rate of 1100-1500 ml/min. giving a filtrate rate of 20-25 ml/min. The concentrated lysate is diafiltered against 10 volumes of 25 mM sodium acetate pH 7.0. This and all subsequent steps in the process can be performed at room temperature.

Hexadecyl-trimethylammonium bromide detergent Treatment:

All polysaccharide serotypes except T7F, T14 and T33F are precipitated with hexadecyl-trimethylammonium bromide (1-4% USP grade 99%). The resulting precipitates are washed with 1% hexadecyl-trimethylammonium bromide in the 25 mM sodium acetate buffer. The resulting precipitate is then resuspended in 0.25M NaCl with the exception of T3 which requires 0.35M NaCl. The solution is clarified by centrifugation or filtration to remove contaminants and then 0.5% KI is added to precipitate excess hexadecyl-trimethylammonium bromide which is subsequently removed by centrifugation or depth filtration.

Anion exchange Chromatography (non-precipitating serotypes only):

Serotypes that do not precipitate with hexadecyl-trimethylammonium bromide (7F, 14, 33F) are subjected to anion exchange chromatography following 1% hexadecyl-trimethylammonium bromide treatment as described above. However, immediately following addition of 1% hexadecyl-trimethylammonium bromide, the polysaccharide mixture is clarified and recirculated through an anion exchange column (50-100ml) and washed with 4-5 volumes of buffer containing 25 mM sodium phosphate pH 7.0. The resulting column effluent is treated with 0.5% KI to precipitate hexadecyl-trimethylammonium bromide.

Activated Carbon Filtration

All serotypes are recirculated through activated carbon filters (CUNO Norit #52s or equivalent) for 30 minutes at 4g carbon/L of crude lysate. The recirculated material is then treated to contain 25 mM sodium phosphate pH 6.8.

Hydroxy apatite (HA) Chromatography

All serotypes are subjected to HA chromatography following CUNO Norit treatment. Materials are recirculated for 30 minutes and the column subsequently washed with 4–5 volumes of buffer containing phosphate.

Final Concentration and Diafiltration

HA column effluent for each of the 23 serotypes is concentrated to 200 ml in a 100K molecular weight cutoff hollow fiber membrane (AG Technologies) with a recirculation rate of 1100–1500 ml/min. giving a filtrate rate of 20–25 ml/min. The concentrated effluent is diafiltered against water for injection until the conductivity is less than 15 μs and subsequently lyophilized.

HPLC polysaccharide quantitation

Samples are injected (40 μl) onto Synchropak GPC-100-Grd GPC-1000-Anly GPC-100-Grd tandem columns at a flow of 0.7 ml/min. eluted with 4% sodium acetate 1 mM EDTA pH 6.7. Polysaccharide content is derived using the appropriate standards and comparing the chromatographic areas detected by refractive index.

FIG. 1 is a representative chromatographic analysis (size exclusion HPLC) of pneumococcal polysaccharide crude lysate form serotype 9V with refractive index detection. Also included are uv absorption values at 260 and 280 nm to reflect approximate nucleic and protein contaminants respectively. This analysis shows high contaminant levels along with a relatively small amount of polysaccharide as evidenced by the small peak closet to the origin (left side of chromatogram). The contaminant levels are expressed as optical density units per gram of polysaccharide (OD/G polysaccharide).

Figure 2:
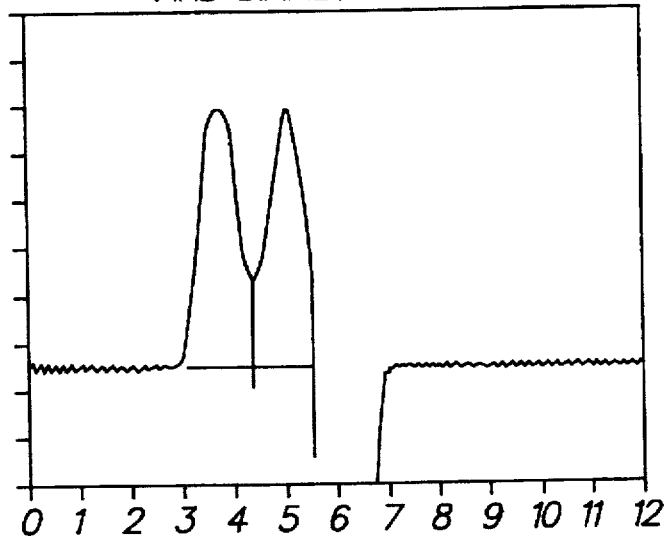
FIG. 2 is a SEC-HPLC analysis of T9V-0012 following 100K concentration and diafiltration.

FIG. 2 illustrates following concentration and diafiltration by ultrafiltration, a 50% decrease in contaminant level is observed for both 260 and 280 nm readings. The HPLC analysis demonstrates a great improvement of the relative purity of the material at this stage of the purification by showing only two major peaks. The peak of interest being nearest the origin.

Figure 3:
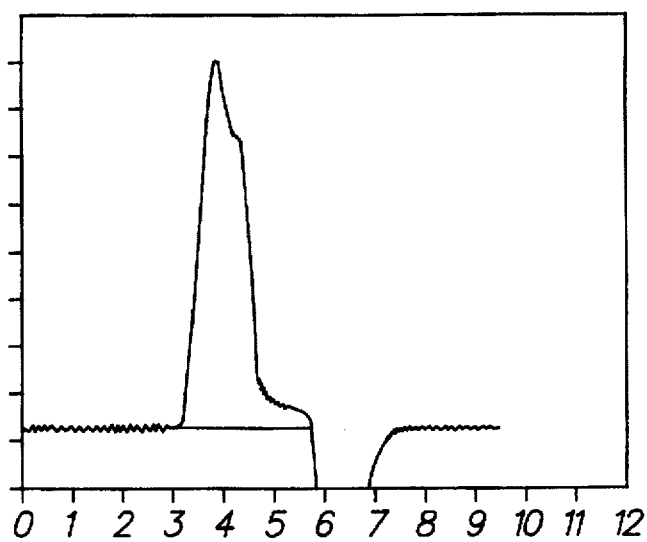
FIG. 3 is a SEC-HPLC analysis of precipitating agent (hexadecyl-trimethylammonium bromide) precipitated T9V-0012.

FIG. 3 illustrates HPLC analysis following hexadecyl-trimethylammonium bromide precipitation revealing a near homogeneous preparation of polysaccharide with approximately 95% removal of contaminants for both protein and nucleic acid readings compared to the crude lysate values.

Figure 4:
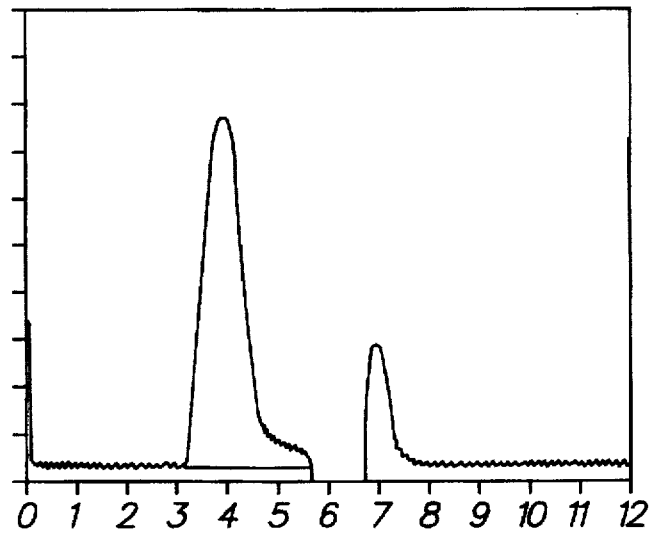
FIG. 4 is a SEC-HPLC analysis of KI treated T9V-0012 precipitate.

FIG. 4 illustrates removal of hexadecyltrimethylammonium bromide by potassium iodide treatment showing an HPLC profile to be one homogeneous peak (small amount of tailing) with minor reduction in protein and nucleic acid contaminants.

Figure 5:
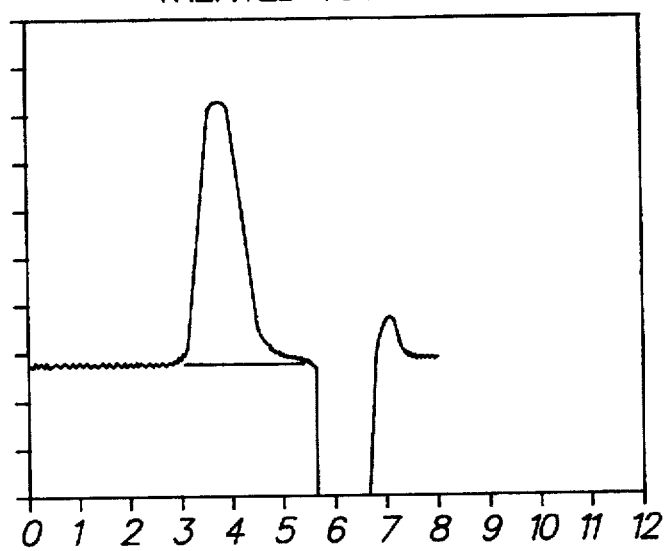
FIG. 5 is a SEC-HPLC analysis of CUNO NORIT (an activated carbon filter) treated T9V-0012.

FIG. 5 illustrates HPLC analysis following activated carbon filtration showing additional minor reduction of the tailing seen in the previous potassium iodide step and additional reduction of protein contaminants.

Figure 6:
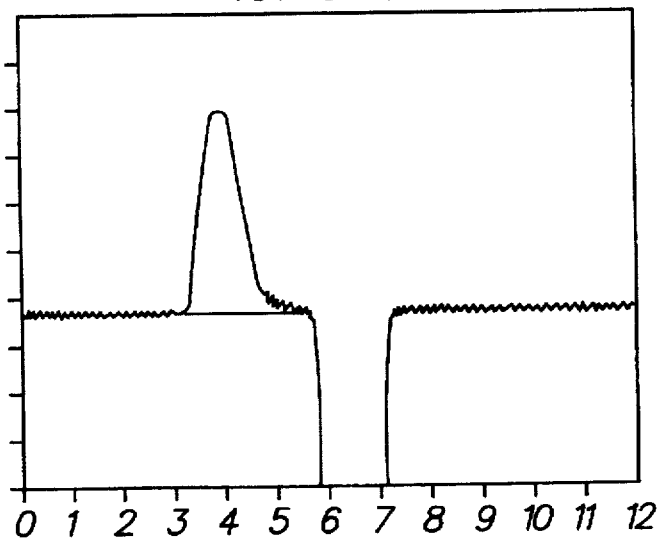
FIG. 6 is a SEC-HPLC analysis of hydroxy apatite purified T9V-0012.

FIG. 6 illustrates the final purification step utilizing ceramic hydroxy apatite which yields a highly purified product as indicated by the HPLC chromatogram and corresponding uv absorbance readings.

FIG. 7 shows the removal of contaminants for T33F-0012 in the modified purification process used for serotypes 7F, 14 and 23F by the inclusion of an anion exchange chromatography step. The top chromatogram shows the polysaccharide solution following hexadecyltrimethylammonium bromide treatment while the bottom chromatogram shows the material following anion-exchange chromatography treatment.

The preparation of raw polysaccharide suspensions which are the fermentation media used in this process are known in the art. Examples of preparations of fermentation media for the 23 serotypes of this process are described in U.S. Pat. Nos. 4,242,501 (1980) and 4,686,102 and are incorporated herein by reference.

The following non-limiting examples illustrate processes of the invention.

EXAMPLE 1

Refer to FIG. 1–6

The purification of one serotype T9V is accomplished using the process outlined by Flowsheet 1. The purity and quality of material purified is monitored by a combination of HPLC and spectrophotometric analyses. Final purity and composition of purified polysaccharide powders are determined by testing procedures that are accepted for vaccines requiring 23 serotypes and found to be satisfactory for all 23 serotypes. A representative chromatographic analysis (size exclusion HPLC) is shown for pneumococcal polysaccharide crude lysate from serotype 9V with refractive index detection. UV absorption values at 260 and 280 nm show approximate nucleic and protein contaminants respectively. This analysis shows high contaminant levels along with a relatively small amount of polysaccharide as evidenced by the small peak closet to the origin. The contaminant levels are expressed as optical density units per gram of polysaccharide (OD/G polysaccharide). Following concentration and diafiltration by ultrafiltration from a starting volume of 2L to a final volume of 0.2L, a 50% decrease in contaminant level is observed for both 260 and 280 nm readings. The HPLC analysis demonstrates a great improvement of the relative purity of the material at this stage of the purification by showing only two major peaks. The peak of interest being nearest the origin. HPLC analysis following hexadecyl-trimethylammonium bromide precipitation reveals a near homogeneous preparation of polysaccharide with approximately 95% removal of contaminants for both protein and nucleic acid readings compared to the crude lysate values. Removal of hexadecyl-trimethylammonium bromide by potassium iodide treatment shows an HPLC profile to be one homogeneous peak (small amount of tailing) with minor reduction in protein and nucleic acid contaminants. HPLC analysis following activated carbon filtration shows additional minor reduction of the tailing seen in the previous potassium iodide step and additional reduction of protein contaminants. The final purification step utilizing ceramic hydroxyapatite yields a highly purified product as indicated by the HPLC chromatogram and corresponding uv absorbance readings. The majority of the purification is performed within the first two steps of the process which include the concentration and diafiltration step and the hexadecyl-trimethylammonium bromide precipitation step. The remainder of the process steps refine the product to adhere to the specifications for vaccines comprising the 23 serotypes of the process.

EXAMPLE 2

Refer to FIG. 7

The purification of serotype T33F-0012 is accomplished using the process outlined by flowsheet 2. The purity and quality of material purified is monitored by a combination of HPLC and spectrophotometric analyses. Clarified crude lysate of T33F-0012 as well as all serotypes is similar in composition to T9V-0012 in terms of purity and HPLC profile. Following concentration and diafiltration by ultrafiltration of T33F-0012 from a starting volume of 2L to a final volume of 0.2L, a 50% decrease in contaminant level is observed for both 260 and 280 nm readings. This is the common observation for all serotypes. HPLC analysis following hexadecyl-trimethylammonium bromide treatment shows a moderate reduction in contaminants (FIG. 7). However, the next step of the process including anion-exchange chromatography removes a large portion of the remaining contaminants bringing the levels low enough to be removed by the remainder of the process which is unaltered from the previous example. Following activated carbon filtration, near complete removal of protein and nucleic acid contaminants is observed. The final purification step utilizing ceramic hydroxyapatite chromatography yields a highly purified product. The majority of the purification is performed within the first step of the modified process for serotypes 7F, 14 and 33F which includes the concentration and diafiltration step. The remainder of the process steps including hexadecyl-trimethylammonium treatment, anion-exchange chromatography, activated carbon filtration and ceramic hydroxyapatite refine the polysaccharide to bring it within the specifications outlined for the 23 valent vaccine.

What is claimed is:

1. An alcohol free process for preparing a purified pneumococcal polysaccharide which comprises:
   (a) lysing with deoxycholate bacterial cells in a fermentation medium containing a S. pneumococcal bacterium of serotype 1, 2, 3, 4, 5, 6B, 8, 9N, 9V, 10A, 11A, 12F, 15B, 17F, 18C, 19A, 19F, 20, 22F or 23F, thereby producing a lysate containing a polysaccharide solution and solid cell debri;
   (b) clarifying the aqueous cell lysate by separating solids from the polysaccharide solution;
   (c) concentrating the polysaccharide solution by ultrafiltration using a 100K molecular weight cutoff membrane to remove low molecular weight contaminants to form a solution of concentrated polysaccharide;
   (d) precipitating the concentrated polysaccharide solution with hexadecyl-trimethylammonium bromide detergent to form a partially purified polysaccharide pellet;
   (e) washing the pellet in buffer which contains hexadecyl-trimethylammonium bromide detergent to remove soluble contaminants;
   (f) collecting the resulting polysaccharide pellet;
   (g) solubilizing the polysaccharide pellet in a saline solution;
   (h) clarifying the polysaccharide solution to remove insoluble protein and nucleic acids;
   (i) adding potassium iodide to the polysaccharide solution to precipitate the hexadecyltrimethylammonium bromide detergent in a hexadecyltrimethylammonium bromide detergent-potassium iodide salt complex;
   (j) clarifying the polysaccharide solution by ultrafiltration; and
   (k) lyophilizing the polysaccharide solution.

2. A process according to claim 1 wherein the polysaccharide pellet of step (g) is solubilized in a 0.15 to 0.35M NaCl solution.

3. A process according to claim 2 wherein the NaCl solution is about 0.25M, the concentration of detergent in step (d) is about 1–2%, the buffer of step (c) is 35 mM sodium acetate and contains 1% detergent and the concentration of potassium iodide of step (i) is about 0.5–1%.

4. A process according to claim 1 wherein the clarifying step (j) comprises:
   (a) filtering or centrifuging the polysaccharide solution to remove the detergent-potassium iodide salt complex;
   (b) filtering the resulting polysaccharide solution through an activated carbon filter;
   (c) adding 25 mM phosphate pH 6.8 to the solution;
   (d) recirculating the polysaccharide solution through a hydroxy apatite column; and
   (e) washing the column with 4 to 5 column volumes of buffer.

5. A process according to claim 4 wherein the filter of step (b) is about 3–5% carbon/0.5 mg/ml polysaccharide.

6. A process according to claim 5 wherein the filter is 4% carbon.

7. An alcohol free process for preparing a purified pneumococcal polysaccharide of pneumococcal bacteria serotypes 7F, 14 or 33F which comprises:
   (a) lysing with deoxycholate bacterial cells in a fermentation medium containing a S. pneumococcal bacterium of serotype 7F, 14 or 33F thereby producing a lysate containing a polysaccharide solution and solid cell debri;
   (b) clarifying the aqueous cell lysate by separating solids from the polysaccharide solution;
   (c) concentrating the polysaccharide solution by ultrafiltration using a 100K molecular weight cutoff membrane to remove low molecular weight contaminants to form a solution of concentrated polysaccharide;
   (d) precipitating the protein and nucleic acid contaminants from the concentrated polysaccharide solution with hexadecyl-trimethylammonium bromide detergent to form a partially purified polysaccharide solution;
   (e) clarifying the polysaccharide solution to remove insoluble nucleic acids and proteins;
   (f) recirculating the polysaccharide solution through an anion exchange column;
   (g) washing the column with 4 to 5 column volumes of buffer;
   (h) adding sodium or potassium iodide to the polysaccharide solution to precipitate the detergent in a hexadecyl-trimethylammonium bromide detergent-potassium iodide salt complex;
   (i) clarifying the polysaccharide solution by ultrafiltration; and
   (j) lyophilizing the polysaccharide solution.

8. A process according to claim 7 wherein the concentration of hexadecyl-trimethylammonium bromide detergent in step (d) is about 1–2%, and the buffer of step (g) is 25 mM sodium acetate, pH 6.8.

9. A process of claim 7 which comprises:
   (a) filtering or centrifuging the polysaccharide solution to remove the hexadecyl-trimethylammonium bromide detergent-potassium iodide salt complex of step (h);
   (b) refiltering the resulting polysaccharide solution through an activated carbon filter;
   (c) adding 25 mM phosphate buffer, pH 6, 8, to the solution;
   (d) recirculating the polysaccharide solution through a hydroxy apatite column; and
   (e) washing the column with 4 to 5 column volumes of buffer.

10. A process of claim 9 wherein the filter of step (b) is about 3–5% carbon/0.5 mg/ml polysaccharide.

* * * * *